United States Patent [19]

Sholder

[11] Patent Number: 4,771,780
[45] Date of Patent: Sep. 20, 1988

[54] RATE-RESPONSIVE PACEMAKER HAVING DIGITAL MOTION SENSOR

[75] Inventor: Jason A. Sholder, Los Angeles County, Calif.

[73] Assignee: Siemens-Pacesetter, Inc., Sylmar, Calif.

[21] Appl. No.: 3,433

[22] Filed: Jan. 15, 1987

[51] Int. Cl.$^4$ .............................................. A61N 1/36
[52] U.S. Cl. ............................. 128/419 PG; 128/782
[58] Field of Search ...... 128/419 B, 419 PG, 419 PS, 128/423 W, 782, 784, 786

[56] References Cited

U.S. PATENT DOCUMENTS

| | | | |
|---|---|---|---|
| 3,204,637 | 9/1965 | Frank et al. | 128/423 W |
| 3,557,796 | 1/1971 | Keller, Jr. et al. | 128/419 PG |
| 3,593,718 | 7/1971 | Krasner et al. | 128/419 P |
| 3,943,936 | 3/1976 | Rasor et al. | 128/419 PS |
| 4,140,132 | 2/1979 | Dahl | 128/419 PG |
| 4,202,339 | 5/1980 | Wirtzfield et al. | 128/419 PG |
| 4,228,803 | 10/1980 | Rickards | 128/419 PG |
| 4,284,986 | 8/1981 | Amortegui | 128/782 |
| 4,428,378 | 1/1984 | Anderson et al. | 128/419 PG |
| 4,436,092 | 3/1984 | Cook et al. | 128/419 PG |
| 4,567,892 | 4/1986 | Plicchi et al. | 128/419 PG |
| 4,596,251 | 6/1986 | Plicchi et al. | 128/419 PG |

Primary Examiner—William E. Kamm
Attorney, Agent, or Firm—Bryant R. Gold

[57] ABSTRACT

A rate-responsive pacemaker includes a motion sensor mounted therein. The output signal from the motion sensor is a digital signal that can be connected directly to the digital processing and control circuits of the pacemaker in order to adjust its basic pacing rate as a function of the physical motion or activity that is sensed. The motion sensor includes an enclosed housing having a conductive element therein that partially fills the space of a cavity within the enclosed housing. The conductive element is free to roll, flow, or otherwise move around the inside of the housing in response to external forces. The external forces that cause the conductive element to move include the physical motion of the patient as well as the force of gravity. As the conductive element moves within the enclosed housing, it makes electrical contact with at least two of three electrodes that are selectively spaced around the inside periphery of the housing. By monitoring whether and for how long an electrical contact is made or broken between electrodes, a determination is thus made relative to the movement of the conductive element within the housing, and the rapidity with which such movement occurs. This sensed motion is directly related to the physical activity or movement of the patient. This signal is processed over time to determine whether and how the pacing rate of the pacemaker should be altered.

9 Claims, 3 Drawing Sheets

RATE-RESPONSIVE PACEMAKER HAVING DIGITAL MOTION SENSOR

BACKGROUND OF THE INVENTION

The present invention relates to implanted pacemakers, and more particularly to an implanted pacemaker that includes a motion or activity sensor for sensing the physical motion or activity of a patient in whom the pacemaker has been implanted.

Pacemakers are used to provide an electrical stimulus to the heart in the absence of normal heart activity in order to keep the heart beating at a safe level. In turn, a heart that beats at a safe level maintains an adequate supply of blood to the body tissue, thereby providing the needed supply of oxygen to the body cells and removing wastes from the body cells—in short, to keep the body cells alive, and hence to keep the patient alive.

As the physiological activity of the patient increases, many of the body cells must work harder, thereby requiring an increased supply of oxygen and an increased removal of carbon dioxide. (Oxygen is the primary fuel or source of energy that is used by the cells as they perform their body function(s), while carbon dioxide is the primary waste product that is expelled from the cells after their work is done.) In a normal healthy person, this increased supply of oxygen is provided by the heart and/or lungs increasing their respective rates of volumetric flow, i.e., by the heart increasing the rate and/or efficiency with which it pumps the blood through the body, and by the lungs increasing the rate and/or efficiency with which they inhale and exhale oxygen and carbon dioxide.

In some patients with a pacemaker, however, the heart may not be able to respond to a physiological need to pump more blood because of the heart's dependency on a stimulus from the pacemaker in order to beat (contract or depolarize). Accordingly, for these pacemaker patients, there is a need to make the pacemaker sensitive to physiological demands so that the pacemaker-provided stimulus can be provided in accordance with these demands. If this need can not be not met, as has often been the case with prior art pacemakers, then the patient must be cautious and limit his or her physical activity so that the physiological demands are kept within safe limits. Unfortunately, this limitation may severely restrict the physical activity of a pacemaker patient.

Recognizing this need, prior art pacemakers have been developed that are programmable, i.e., the basic rate at which the stimulation pulses are provided by the pacemaker can be noninvasively changed to suit the particular needs of the patient. However, even programming, while extremely useful in many ways, has not been totally satisfactory because it still requires that a programming change be made, and such changes can typically only be made by a physician or other technician having the proper equipment. Moreover, even if the patient has access to the proper programming equipment, the patient can not always know when his or her physiological demands will be changing. Hence, there is a need in the art to provide a pacemaker that automatically responds to the physiological demands of the patient so that the needed pacemaker-provided stimuli can be provided at the appropriate times and at the appropriate rates.

Automatic physiologically responsive pacemakers are known in the art. Such pacemakers have relied on numerous and varied sensed parameters as a physiological indicator that the demands of the patient are changing. For example, it is known in the art to measure blood temperature (see U.S. Pat. No. 4,436,092), blood oxygen concentration (see U.S. Pat. No. 4,202,339), repolarization interval (see U.S. Pat. No. 4,228,803), respiration rate (see U.S. Pat. Nos. 3,593,718 and 4,567,892), minute ventilation (see U.S. Pat. No. 4,596,251), and physical activity as sensed by a piezoeletric element (see U.S. Pat. Nos. 4,140,132 and 4,428,378) as parameters that indicate a change in physiological need. Further, the applicant is aware of proposals to measure the depolarization interval (see pending U.S. application Ser. No. 716,831, filed 03/27/85) and to use various mechanical devices in conjunction with acoustic sensing equipment in a pending German application in order to determine the physiological demands of a patient so that the stimulation rate of the pacemaker can be adjusted accordingly.

For purposes of the present invention, it is the physical activity of the patient, as sensed by measuring the motion or movement of the patient, that comprises the physiological parameter to be used for controlling the rate of a pacemaker.

As indicated above, some attempts are known in the art for causing a pacemaker to sense and respond to physical activity. Using a piezoelectric element, as is taught in the U.S. Pat. No. 4,428,378 for example, requires that the electrical analog signal from the piezoelectric element be processed in a prescribed manner. While such processing can be done, it requires special filtering and thresholding circuitry, all of which adds to the bulk and power consumption of the pacemaker. Needless to say, keeping power consumption and size to a minimum is a primary goal of all implantable pacemaker design. Hence, any added circuits which tend to increase the size, bulk, or power consumption of a pacemaker are disfavored.

Further, there are other disadvantages to using a piezoelectric element as a sensor of physical activity. For example, the physical construction of a piezoelectric element makes it somewhat direction dependent. Hence, depending upon how it is oriented within the patient, it may be less sensitive to physical movement in a given direction (X, Y or Z axis) than to movement in another direction. Further, whenever an analog signal is sensed, such as the signal from a piezoelectric element, it usually must eventually be converted to some sort of digital signal that can interface with the basic digital circuits used to realize modern pacemaker circuits. While analog-to-digital circuits are well known in the art, they too add to the bulk and power consumption of the pacemaker.

Where an acoustic pickup device is employed in conjunction with a mechanical device, which mechanical device is designed to generate various sounds as a function of physical activity, such as is disclosed in the above-mentioned German patent application, an analog-to-digital conversion must still occur. Further, an added element (the mechanical device that serves as the source of the acoustic signal and/or the microphone pickup element) must be included within the pacemaker.

Accordingly, what is needed is a way of detecting physical activity or body motion using a simple detector device that can interface directly with the digital circuits of the pacemaker and that does not noticeably add to the complexity, bulk, or power consumption of the pacemaker.

Finally, it is noted that even though a dual chamber pacemaker (i.e., one that can provide stimulation pulses to both chambers of the heart) may theoretically be operable in a mode that is responsive to the physiological demands of some patients, there may be practical reasons why such a dual chamber pacemaker is not used. For example, in a patient with complete heart block, a dual chamber pacer operating in the DDD mode of operation (i.e., the pacemaker paces in both the atrium and ventricle, and senses in both the atrium and ventricle) will respond to the heart's natural pacemaker—the SA (Sinoatrial) Node. This occurs because the atrium responds to the SA Node and causes the atrium to contract. The atrial sensing circuits of the DDD pacemaker sense this contraction and, after an appropriate AV delay, generate a ventricular stimulation pulse that causes the ventricle to contract. Thus, the DDD pacer guarantees rate responsiveness and AV synchrony. However, as indicated, there may be some circumstances where a DDD pacemaker would not be used. Hence, for these patients, there is still a need for a single chamber pacemaker that is automatically responsive to the patient's physiological needs.

In the description of the invention that follows, it is noted that in general no distinction will be made between whether a single chamber or a dual chamber pacemaker is used. This is because the motion or activity sensor described herein can be used with either type of pacemaker.

SUMMARY OF THE INVENTION

The present invention is directed to an implantable pacemaker (or other implanted medical device) that includes a body motion sensor as a part thereof. Using the output from the motion sensor as an indicator of the patient's physiological need, the rate at which the pacemaker provides stimulation pulses to the heart can be appropriately adjusted.

The motion sensor of the present invention provides a digital signal as an output signal. The frequency or period of this digital signal represents the motion activity of a patient to whom the sensor is attached. Thus, this signal can be connected directly into the digital processing circuits of the medical device with which it is used without the need for using additional analog-to-digital conversion circuits.

The motion sensor comprises a sealed housing having a cavity therein into which an electrically conductive element is placed. This electrically conductive element does not fill the cavity and is allowed to freely roll or move therein when subjected to external forces, such as the force of gravity, or any movement of the patient. Protruding into the cavity is a plurality of electrodes, each of which respectively makes electrical contact with the conductive element whenever the conductive element moves thereby, and each of which is electrically accessible from a point exterior to the housing. The size of the conductive element and the construction of the cavity in which it is placed are such that the conductive element makes momentary electrical contact with at least two electrodes simultaneously. Thus, by making appropriate electrical connections to the electrodes from the outside of the housing, a determination can be made as to the position of the conductive element within the housing relative to the position of the electrodes. More significantly, by monitoring the electrodes external to the housing, a determination can be made as to any movement of the conductive element within the housing and the rapidity with which the movement occurs. which movement is directly related to the physical motion or activity to which the sensor is subjected.

By placing a sensor as above described within or on the patient, the detected movement of the conductive element can thus be used as an indication of the physical motion of the patient. This is because the external forces that act upon the conductive element to cause it to move include the physical motion of the patient. That is, in operation, the conductive element always moves to a position closest to the earth's gravitational pull by the gravity forc vector. The conductive element is forced away from this position by any motion of the patient not in perfect alignment with the gravity force vector. Because the motion of the patient, whether walking, talking, running, or merely breathing, will only be in alignment with the gravity vector, if at all, for extremely short periods of time, it is possible by monitoring the motion of the conductive element over time to obtain an accurate indication of the patient's motion. Further, by suitably processing the signals generated by such a sensor, it is generally possible to distinguish, and therefore separate, those signals caused by external forces that do not include the physical motion of the patient.

Advantageously, the physical movement of the patient in any direction (x, y or z axis) can be detected by the physical motion sensor of the present invention (providing none of these axes are in perfect alignment with the gravitational vector). Further, through appropriate electrical connections, the sensor generates a pulse-type signal (pulse train) in response to the sensed physical movement that is directly compatible with the pacemaker's digital circuits. Hence, no analog-to-digital conversion, or other analog filtering is required before the signal can be digitally processed. The frequency of occurrence, or more precisely the time period between successive pulse of the pulse train signal, provides an indication of the magnitude of the sensed physical motion.

From the above summary, it is thus seen that a primary feature of the present invention is to provide an implantable pacemaker that includes a physical motion sensor. The rate at which the pacemaker provides stimulation pulses to the heart, or the length of an escape interval (in the case of a demand-type pacemaker), is then varied in response to physical motion sensed by the motion sensor. Thus, through use of the motion sennnsor the pacemaker is made physiologically responsive to physical motion.

Another important feature of the present invention provides a motion sensor for use with a medical device that reliably signals the physical movement or activity of a patient to whom the motion sensor is attached. In a preferred embodiment, the indication providedby the sensor is a pulse signal that is compatible for use with digital circuits without the need for analog-to-digital conversion, buffer, or threshold circuits. Further, the sensor consumes little, if any, additional power beyond that of the pacemaker circuits. The sensor is advantageously small in size and can be readily included within the housing of a typical pacemaker or other implantable medical device.

BRIEF DESCRIPTION OF THE DRAWINGS

The above and other advantages and features of the present invention will be more apparent from the following more particular description thereof, presented in conjunction with the following drawings, wherein.

DETAILED DESCRIPTION OF THE INVENTION

The following description is of the best presently contemplated mode of practicing the invention. This description is not to be taken in a limiting sense but is made merely for the purpose of describing the general principles of the invention. The scope of the invention should be ascertained with reference to the appended claims.

Figure 1:
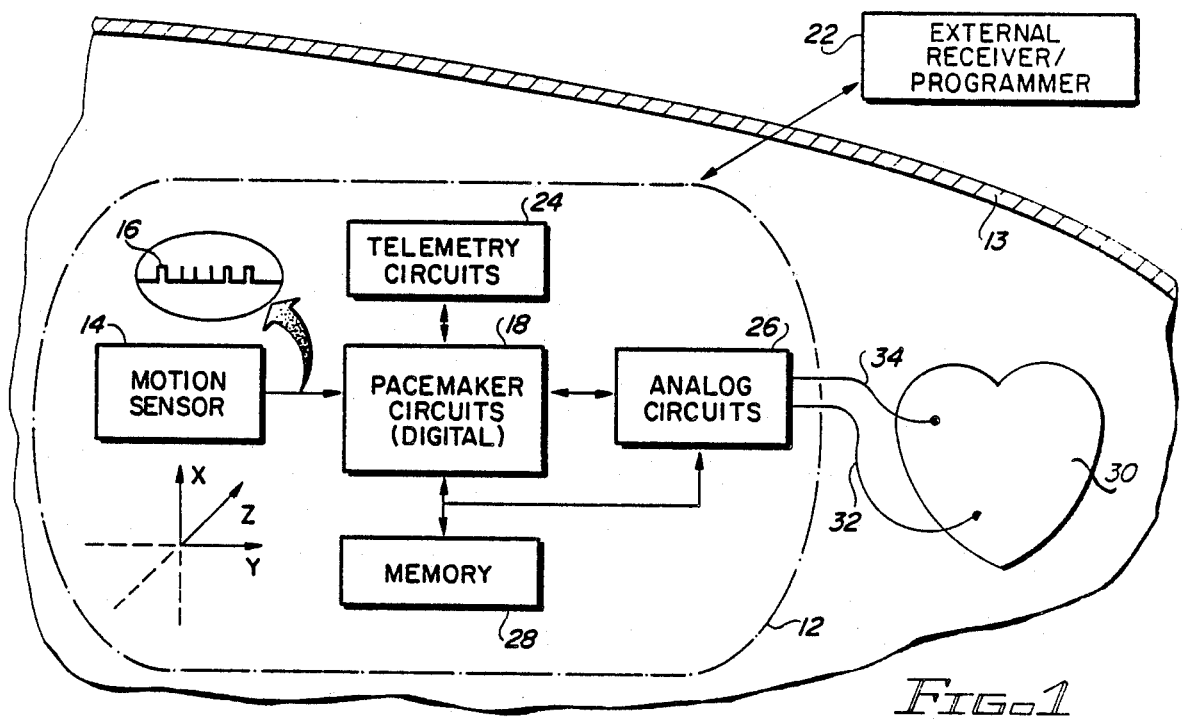
FIG. 1 is a block diagram of a pacemaker having a physical motion sensor in accordance with the teachings of the present invention.

Referring first to FIG. 1, there is shown a block diagram of an pacemaker 12 that is implanted beneath the skin 13 of a patient. The pacemaker 12 includes a motion sensor 14. Any motion sensed by the sensor 14 is manifest by a digital signal 16 that is fed directly into the digital circuits 18 of the pacemaker. The digital circuits 18 determine when a stimulation pulse should be generated. Operating parameters that control when such a stimulation pulse is to be generated, in addition to the motion signal 16 (described more fully below), include control signals received from an external programmer through telemetry circuits 24, and cardiac activity sensed by analog circuits 26. Many of the control signals received through telemetry circuits 24 are stored in memory 28, as are other controlling parameters. In addition to being able to receive program control signals from the external programmer, the pacemaker 12 can also send signals through the telemetry circuits 24 that are received by an external receiver. As shown in FIG. 1, the external programmer and eternal receiver are typically combined into a single receiver/programmer device 22.

When the pacemaker circuits 18 have determined that a stimulation pulse is to be generated, a trigger signal is presented to the analog circuits 26. The analog circuits 26 respond to this trigger signal by generating a stimulation pulse of predetermined amplitude that is delivered to the heart 30 via lead 32 or 34. (It is noted that while two leads, 32 and 34, are shown in FIG. 1, for many applications only one lead would be required.)

With the exceptions as indicated below, the pacemaker 12 in FIG. 1 operates in conventional manner. Hence, in the description that follows, no additional detail will be provided relative to its operation, except with respect to how the digital pacemaker circuits 18 respond to the motion signal 16 generated by the sensor 14. Before explaining this response, however, it will be helpful to describe the sensor 14 and the manner in which the digital motion signal 16 is generated.

Figure 2:
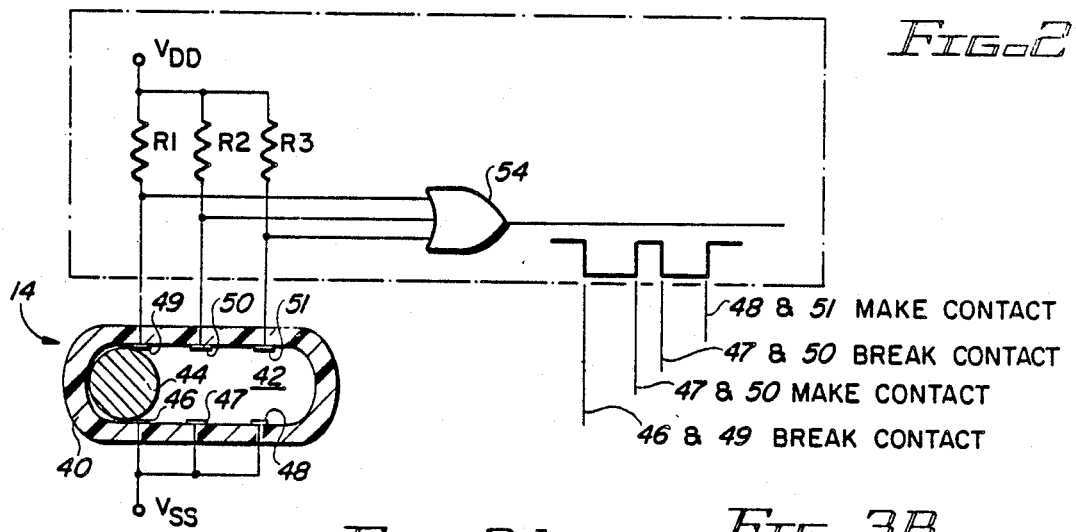
FIG. 2 is a simplified diagram of the motion sensor of the present invention.

Referring to FIG. 2, a simplified one-dimensional version of the sensor 14 is presented in order to explain the basic operating principles thereof. The sensor includes an enclosed housing 40 having a cavity 42 therein. This housing is made from a non-conductive material, such as glass. Inside the housing 40, within the cavity 42, a conductive element 44 is placed. This conductive element is allowed to freely move within the housing 44 as it is subjected to external forces, such as the force of gravity or forces caused by motion of the sensor 40. In the preferred embodiment, the cavity 42 is evacuated of all gases, i.e., it is a vacuum, and the conductive element 44 is a bead of liquid mercury. Any conductive material, whether a solid, liquid, or gas, could of course be used for this purpose so long as it moves within the cavity 42 when subjected to external forces. As the housing is tilted or otherwise moved due to the motion of the patient. the force of gravity (sometimes referred to herein as the gravity vector) causes the conductive element 44 to roll, flow, or slide to its lowest possible point within the cavity 42. As the patient moves in any direction not in perfect alignment with the force of gravity, forces are generated according to well-established laws of physics that force the conductive element 44 away from this lowest point.

Protruding into the cavity 42 are a plurality of electrodes. Six such electrodes 46-51 are shown in the drawing. The conductive element is sized, and the electrodes are spaced apart, such that the conductive element always makes momentary simultaneous contact with at least two of the electrodes.

To illustrate, in the simplified drawing of FIG. 2, the conductive element 44 is shown in electrical contact with electrodes 46 and 49. If the housing 40 were tipped so that the right side thereof became lower than the left side, thereby causing the force of gravity to move the conductive element 44 from the left to the right of the housing, or if some other force were applied so as to cause the conductive element to move left-to-right, the conductive element 44 would in sequence break the contact between electrodes 46 and 49, make and break contact with electrodes 47 and 50, and then make contact with electrodes 48 and 51. If electrodes 46-48 are externally connected to a common voltage potential Vss, and if electrodes 49-51 are each externally connected to a voltage potential Vdd through respective pull-up resistors R1-R3, and if each electrode 49-51 is also connected as an input to an OR gate 54, the output signal of OR gate 54 represents the motion of the conductive element 44 from the left side of the housing 40 to the right side. That is, as shown in FIG. 1, the signal will first be high (at the Vdd level) representing the making of contact between electrodes 46 and 49. It will then go low, representing the breaking of the contact between electrodes 46 and 49. It then goes high again, representing the making of contact between electrodes 47 and 50; and then goes low again, representing the breaking of contact between electrodes 47 and 50. Finally, it goes high, representing the making of contact between electrodes 48 and 51.

When the housing 40 is alternately titled or otherwise moved such that the left side is alternately higher and then lower than the right side, the gravity vector causes the conductive element 44 to move first left-to-right and then right-to-left within the cavity 42. Other force could be applied to cause this same back and forth motion. In either event, such back and forth motion of the conductive element 44 causes a train of pulses to be generated at the output of gate 54. The width of the pulses and the interpulse spacing (time interval between adjacent pulses) are representative of the velocity of the conductive element 44 as it so moves.

It is noted that the OR gate 54 and pull-up resistors R1–R3 shown in the simplified diagram of FIG. 2, may comprise part of the digital logic circuits 18 of the pacemaker 12. As is known to those skilled in the art, the pull-up resistors R1–R3 may be very large in value, thereby keeping current flow to a minimum. Moreover, where CMOS circuits are used for the digital logic elements of the digital circuits, the equivalent of the pull-up resistors R1–R3 may be realized using other CMOS components, thereby effectively reducing any power consumption associated with the sensor 14 to extremely low values.

Figure 3A:
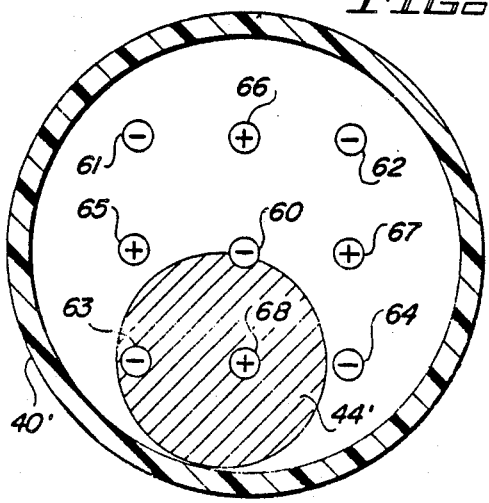
FIG. 3A is a cross-sectional view of a preferred embodiment of the motion sensor of the present invention.
Figure 3B:
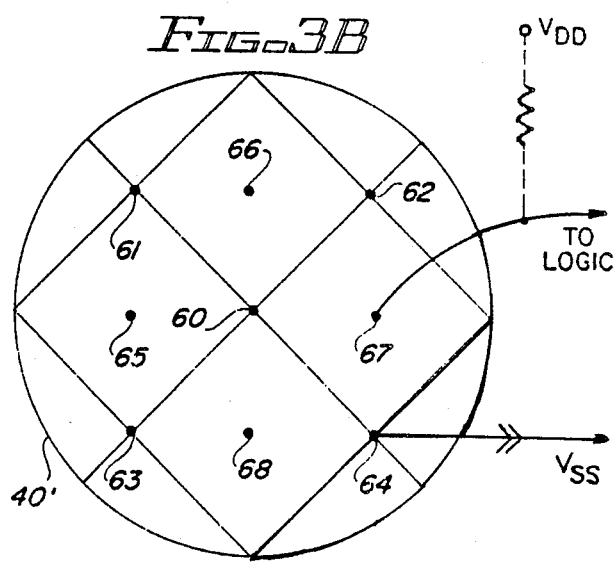
FIG. 3B is an outside view of the motion sensor of FIG. 3A.

Referring next to FIGS. 3A and 3B, a preferred construction of the sensor 14 is illustrated. In FIG. 3A, which is a cross-sectional view of the sensor, the housing 40' is a hollow sphere made from glass or other suitable non-conductive material. Selectively spaced around the periphery of the sphere housing 40' is a matrix of spaced-apart electrodes 60–68, only a portion of which are shown in the figure. Inside of the sphere a conductive element 44' is allowed to roll or flow. The preferred material for the conductive element 44' is mercury. As is known in the art, for all temperatures of concern, mercury is a liquid.

The rolling or movement of the conductive element 44 can be detected by connecting the electrodes in a scheme such as that shown in FIG. 3B where the electrodes 60–64 are connected to a common reference potential Vss, and the electrodes 65–68 are connected to a different reference potential Vdd through respective pull-up resistors, or equivalent. (Thus, in FIG. 3A, the electrodes 60–64 are labeled "−", indicating they are tied to Vss, the most negative potential; and electrodes 65–68 are labeled "+", indicating they are coupled to Vdd, the most positive potential.) The "+" electrodes 65–68 are then also connected to the appropriate logic circuits. Whenever the voltage potential at a given electrode 65–58 is pulled to the Vdd potential, that indicates a connection has been broken between that electrode and an adjacent "−" electrode. Similarly, whenever the voltage potential at a given electrode 65–68 is pulled to the Vss potential, that indicates a connection has been made between that electrode and an adjacent "−" electrode by the conductive element 44' within the spherical housing 40'. Thus, by monitoring the "+" electrodes at the logic circuitry, as described in connection with FIG. 2, a signal is generated indicating the motion of the conductive element 44'. Advantageously, this signal can be applied directly to the logic circuits without the need for any analog-to-digital conversion, threshold detection, or other analog processing.

As mentioned previously, the pulse width and interpulse interval (i.e., the period) of the pulse train generated by the sensor 14 of the present invention provide a measure of the physical motion of the patient. This is because the force of gravity causes the conductive element 44' to be pulled to its lowest possible position within the housing 40'. If the patient were able to hold perfectly still, without any motion whatsoever, the conductive element 44' would not move away from this rest position. (The term "rest position" is used herein to indicate that position to which the conductive element is forced by the gravity vector.) However, any physical activity or motion of the patient, no matter how slight, causes other forces to be generated that displace the conductive element 44' away from its rest position. The more vigorous the motion of the patient, the larger these forces become, thus causing the conductive element 44' to roll or move more rapidly within the housing 40'. This more rapid movement is reflected in a motion signal 16 having narrower pulse widths and a shorter interval between pulses.

The digital circuitry 18 processes the motion signal 16, using conventional techniques, in order to determine whether the signal has a high frequency (period) or short pulse width, or both. If so, a determination is made that the patient has begun a high activity phase. However, before altering the operation of the pacemaker, the digital circuits monitor the sensed activity to determine if this high activity phase continues over a prescribed period of time. For example, a short burst of a high frequency motion signal could be caused by something or someone simply bumping into the patient, and there would generally be no need to adjust the pacemakers's operation. However, if the high frequency motion signal continues for a prescribed period of time, such as 30–45 seconds, then the patient is probably moving more vigorously than normal, and an adjustment of the pacemaker's pacing rate (which includes adjusting the escape interval of a demand-type pacemaker) is in order.

The sensor 14 of the present invention, as indicated, responds to all motion of the patient, even talking and breathing. However, these lower-level motion activities can be distinguished because they will have an average frequency and/or pulse width associated therewith that can be detected. In operation, the digital processing circuits 18 will recognize this lower-level type of activity or motion and simply save it as a reference level. This reference level could, of course, change over a period of time. This reference level (and by "reference level" it is meant the frequency or period and/or average pulse width of the motion signal) could then be compared against the present motion signal level in order to determine if any significant changes exist that have been maintained for the requisite time period. If so, appropriate adjustments could be made, upward or downward as required, in the basic pacing rate set by the pacemaker.

While the invention described herein has been described with reference to a particular embodiment and application thereof, numerous variations and modifications could be made thereto by those skilled in the art without departing from the spirit and scope of the invention as claimed. Accordingly, the true scope of the invention should be determined with reference to the claims set forth below.

What is claimed is:

1. A rate-responsive pacemaker (12) for providing stimulation pulses to a patient's heart at a rate that varies as a function of physical motion of said pacemaker, said pacemaker comprising:

first circuit means (18) for generating a timing signal at a time when a stimulation pulse is to be generated by said pacemaker;

second circuit means (26) responsive to said timing signal for generating said stimulation pulse;

lead means (32, 34) connected to said second circuit means for delivering said stimulation pulse to a desired location; and sensor means (14) for sensing the physical motion of said pacemaker and for generating a digital motion signal (16) indicative of said sensed physical motion, said digital motion signal having pulse widths and intervals between pulses that vary as a function of the sensed physical motion of the pacemaker; and for providing said digital motion signal to said first circuit means.

2. The pacemaker of claim 1 wherein said sensor means comprises:

a plurality of electrodes connected to said first circuit means;

means for making and breaking electrical contact with said plurality of electrodes as said sensor means is subjected to physical motion.

3. The pacemaker of claim 2 wherein said means for making and breaking electrical contact with said plurality of electrodes comprises a movable conductive element enclosed within a housing, said housing having an inside wall, a portion of said electrodes being exposed on the inside wall, said conductive element making momentary simultaneous electrical contact with at least two of said electrodes as said conductive element moves within said housing, said housing being affixed to said pacemaker, the movement of said pacemaker causing said conductive element to move within said housing.

4. The pacemaker of claim 3 wherein said conductive element within said housing comprises a liquid.

5. The pacemaker of claim 4 wherein said liquid conductive element comprises mercury.

6. The pacemaker of claim 3 wherein said conductive element within said housing of said sensor means comprises a solid.

7. In a rate-responsive pacemaker having means for generating a stimulation pulse, means for delivering said stimulation pulse to a desired cardiac tissue location, physiological sensing means for sensing a physiological parameter; and adjustment means for adjusting the rate at which said pacemaker generates said stimulation pulses as a function of the physiological parameter sensed by said physiological sensing means; said physiological sensing means comprising a motion sensor affixed to said pacemaker that includes:

a plurality of electrodes;

means responsive to the application of external forces for making and breaking electrical contact between at least two of said plurality of electrodes; and means for monitoring said electrodes for determining when electrical contact exits therebetween.

8. The rate-responsive pacemaker of claim 7 wherein said making and breaking electrical contact means of said motion sensor comprises a housing having an inner wall, a movable conductive element enclosed within said housing, said housing having a portion of each of said plurality of electrodes exposed on the inner wall thereof, said exposed electrodes being spaced apart a first prescribed distance, said conductive element having a size relative to said first prescribed distance such that said conductive element makes simultaneous electrical contact with at least two of said electrodes as said conductive element is moved within said housing by the application of external forces.

9. The rate-responsive pacemaker of claim 8 wherein the housing of said motion sensor comprises a generally spherically-shaped housing having a corresponding spherically-shaped cavity therein in which said conductive element may move in response to external forces in any direction.

* * * * *